United States Patent
Horinouchi et al.

(10) Patent No.: US 11,795,524 B2
(45) Date of Patent: Oct. 24, 2023

(54) MEDICAL PT-W ALLOY

(71) Applicant: TANAKA KIKINZOKU KOGYO K.K., Tokyo (JP)

(72) Inventors: Yuki Horinouchi, Isehara (JP); Michimasa Okubo, Isehara (JP); Mizuki Nihei, Isehara (JP); Akira Inoue, Isehara (JP); Takeyuki Sagae, Isehara (JP)

(73) Assignee: TANAKA KIKINZOKU KOGYO K.K., Tokyo (JP)

( * ) Notice: Subject to any disclaimer, the term of this patent is extended or adjusted under 35 U.S.C. 154(b) by 0 days.

(21) Appl. No.: 17/940,965

(22) Filed: Sep. 8, 2022

(65) Prior Publication Data

US 2023/0087651 A1 Mar. 23, 2023

(30) Foreign Application Priority Data

Sep. 13, 2021 (JP) .................. 2021-148529

(51) Int. Cl.
*C22C 5/04* (2006.01)
*A61L 31/02* (2006.01)
*A61L 31/14* (2006.01)

(52) U.S. Cl.
CPC .............. *C22C 5/04* (2013.01); *A61L 31/022* (2013.01); *A61L 31/143* (2013.01)

(58) Field of Classification Search
CPC ..................................... C22C 5/04; C22F 1/14
See application file for complete search history.

(56) References Cited

U.S. PATENT DOCUMENTS

| | | | |
|---|---|---|---|
| 2017/0226362 A1 | 8/2017 | Fratello et al. | |
| 2021/0069387 A1 | 3/2021 | Chen et al. | |

FOREIGN PATENT DOCUMENTS

| CN | 109385591 A | 2/2019 |
|---|---|---|
| JP | 2005-233967 A | 9/2005 |
| JP | 2006-129935 A | 5/2006 |
| JP | 2016-130351 A | 7/2016 |
| JP | 2020-111795 A | 7/2020 |

OTHER PUBLICATIONS

Extended European Search Report issued in corresponding European No. 22184685, dated Dec. 14, 2022.
Umeda M., et al., "Methanol electrooxidation at Pt-Ru-W sputter deposited on Au substrate," Journal of Power Sources, Elsevier, Amsterdam, NL, vol. 136, No. 1,Sep. 10, 2004, pp. 10-15, XP004544508, ISSN: 0378-7753, DOI: 10.1016/J.JPOWSOUR. 2004.05.013 Section 2(c) Pt-W, figure 1.
Chinese Office Action issued in connection with CN Appl. Ser. No. 202210967349.7 dated May 27, 2023.

*Primary Examiner* — Jessee R Roe
(74) *Attorney, Agent, or Firm* — Foley & Lardner LLP

(57) ABSTRACT

The present invention relates to a medical Pt—W alloy, containing 10 mass % or more and 15 mass % or less of W, with the balance being Pt and inevitable impurities, in which a Zr content is 1000 ppm or less. Limiting the Zr content can improve workability, particularly workability at the stage of hot working. Regarding impurity control, further limiting a Ca content to 250 ppm or less can provide more suitable workability. The present invention is good in workability in processing into a wire included in an embolic coil, a guide wire or the like.

5 Claims, 1 Drawing Sheet

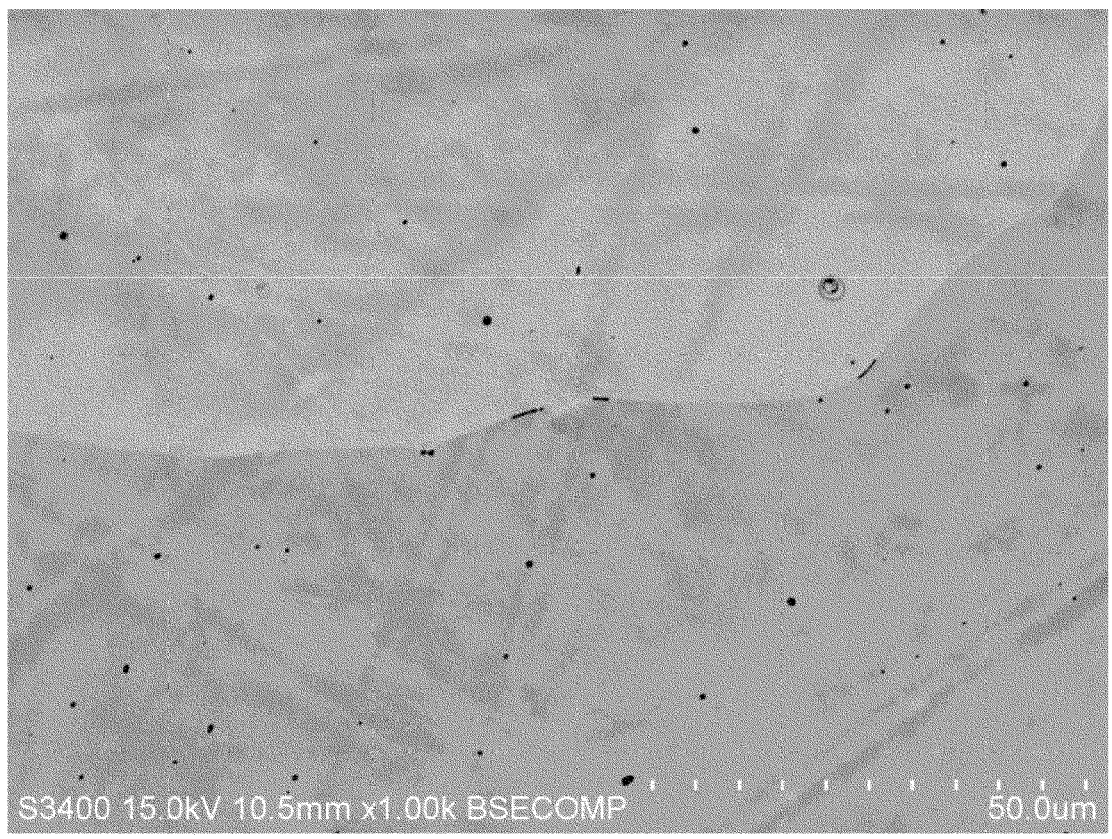

MEDICAL PT-W ALLOY

CROSS-REFERENCE TO RELATED APPLICATIONS

This application claims priority to Japanese Application No. 2021-148529, filed on Sep. 13, 2021. The content of this application is hereby incorporated by reference in its entirety.

BACKGROUND OF THE INVENTION

Field of the Invention

The present invention relates to a medical Pt alloy suitably used as a constituent material of a medical tool such as an embolic coil or a guide wire. More particularly, the present invention relates to a Pt—W alloy containing W in a predetermined range and being excellent in workability in processing into a wire or the like.

Description of the Related Art

As constituent materials of various medical tools such as a stent, a catheter, a guide wire and an embolic coil, various metal materials such as a Pt alloy, a Ti alloy, and stainless steel have been conventionally applied. A medical metal material is required to have various properties such as biocompatibility and mechanical strength.

A medical tool is used in a state in direct contact with a human body, and an embolic coil or the like may be embedded in a human body. Therefore, a constituent material of such a tool needs chemical stability (corrosion resistance). Besides, some metals acquire an allergic property through a bond to a protein present in a human body, and hence it is necessary to exclude such metals. In consideration of these factors, a medical material is required to have affinity/compatibility with a human body.

Further, medical tools such as an embolic coil retained within a pulsating/beating blood vessel, and a guide wire moving in a bending blood vessel with repeated deformation are also required to have mechanical properties such as strength and a spring property. In addition, in a treatment using such a medical tool, the position of the tool in a human body is usually checked by X-ray photography, and hence a metal material having X-ray visibility is suitably used.

Metal materials such as a Pt alloy, a Ti alloy and stainless steel possess properties meeting these various requirements, and a material is selected from these in accordance with the shape or use conditions of a medical tool. Here, as an alloy material suitably used for a medical tool, such as an embolic coil or a guide wire, used with an extra fine metal wire formed into a coil shape, a Pt—W alloy is known. For example, Patent Document 1 discloses a guide wire made of a Pt—W alloy wire having a W concentration of 3 mass % or more and 15 mass % or less.

PRIOR ART DOCUMENT

Patent Document

Patent Document 1: Japanese Patent Application Laid-Open No. 2006-129935

A Pt—W alloy is used in a metal wire included in an embolic coil, a guide wire or the like because of its mechanical properties. An embolic coil is a tool to be retained in a blood vessel, in a treatment of a cerebrovascular disease, for preventing rupture of a cerebral aneurysm. A guide wire is a tool used for guiding a catheter in a catheter treatment. Such a medical tool needs to exhibit a perfect and accurate behavior in use and within a human body, and hence high strength and high spring property are particularly significant. A Pt—W alloy is a Pt alloy having high strength owing to addition of W, and is known as an alloy excellent in the mechanical properties.

In addition, a Pt—W alloy has suitable properties in X-ray visibility and biocompatibility. Pt and W are metals having a high atomic weight, and a Pt—W alloy of these metals have good X-ray visibility. Furthermore, Pt, which is a precious metal, is well known to have very high chemical stability, and W is also a stable metal, and hence, a Pt—W alloy is also advantageous in minimally affecting a human body.

SUMMARY OF THE INVENTION

Technical Problem

A constituent material of an embolic coil, a guide wire or the like is, however, required to have high workability in addition to biocompatibility and mechanical properties. Such a medical tool is produced by processing/molding an extra fine metal wire, and hence workability in processing performed till obtaining a wire is significant. A metal wire is generally produced from an alloy ingot through a combination of hot working and cold working. A hot working step is a step significant for breaking a cast structure in a casted alloy ingot by hot forging, hot swaging or the like, and for processing the alloy ingot into a dimension for cold working performed thereafter. Besides, a cold working step is a step necessary for obtaining a final shape as a wire by cold rolling (groove rolling), wire drawing and the like. At a stage of these processing, a crack or disconnection of a material to be processed should be avoided. This is because merely a small crack is unacceptable in a medical tool, such as an embolic coil or a guide wire, to be inserted/retained into/in a human body.

Regarding a Pt—W alloy, a wire having a requested wire diameter can be somewhat obtained by optimizing processing conditions. According to examination made by the present inventors, however, a conventional Pt—W alloy is not always stably processed, and a crack may be caused in a material to be processed in some cases. Such a processing crack is sometimes caused at a stage of hot working where processing resistance is comparatively low. When a crack is caused in hot working, the resultant cannot be subjected to cold working, which can be an obstacle in efficient production of an alloy wire.

In recent years, wires for medical tools are demanded to be extra fine, and are required to be processed with higher processing accuracy in more cases. Under this background, it should be said that there is a room of improvement in workability of a Pt—W alloy. Therefore, an object of the present invention is to provide a Pt—W alloy that is suitable for various medical tools, possesses mechanical properties, biocompatibility, X-ray visibility and the like, and is excellent in workability.

Solution to Problem

For solving the above-described problems, the present inventors decided to verify a cause of occurrence of a crack or the like in a processing step of a Pt—W alloy based on a raw material and whole production procedures. As a result, it was found that there is a possibility of workability degradation by Zr (zirconium) mixed in the alloy during the production procedures.

A Pt—W alloy is an alloy of which mechanical properties are improved by solid-solution strengthening through addition of W to Pt. When Zr is mixed in this Pt—W alloy, Zr precipitates, in the form of an oxide ($ZrO_2$), on the grain boundary and in the crystal grain of an alloy parent phase. Since Zr is not basically an intended additional element, even when it is mixed, the amount is very small, and the oxide is probably so minute that it is difficult to visually recognize in structure observation. The present inventors presumed that this minute precipitate of Zr affects toughness of the alloy, and causes a crack even at the stage of hot working.

There seems to be several routes of Zr mixture in a Pt—W alloy. The present inventors presumed that influence of the mixture in a casting step is large, and as a result of earnest studies, found an effect of reducing a Zr content in the alloy and a resultant effect of improving workability, and thus, conceived the present invention.

Specifically, the present invention is drawn to a medical Pt—W alloy containing mass % or more and 15 mass % or less of W, with the balance being Pt and inevitable impurities, in which a Zr content is 1000 ppm or less. Now, the medical Pt—W alloy of the present invention will be described in detail.

The medical Pt—W alloy of the present invention is a Pt—W alloy having a W concentration of 10 mass % or more and 15 mass % or less. The element W is an additional element for improving mechanical properties such as strength (tensile strength) of the alloy. As described above, material strengthening by W derives from solid-solution strengthening, and as the amount of W to be added increases, the strength increases. A lower limit of the W concentration is set to 10 mass % in the present invention because strength preferable as a medical tool such as a guide wire cannot be ensured when the concentration is less than 10 mass %.

On the other hand, when the W concentration is too high, the strength becomes excessively high, which affects workability. Degradation of workability caused when the W concentration is beyond 15 mass % is, however, caused by hardening of an alloy parent phase, and is different from degradation of workability caused by Zr. Besides, the influence occurring when the W concentration is beyond mass % more affects, as compared with workability in processing mainly into a wire or the like (primary processing), workability in further processing the wire or the like (secondary processing). A guide wire, an embolic coil or the like is produced by processing a wire into a coil shape or the like. When the W concentration is beyond mass %, a defect such as a crack easily occurs in the coiling processing or the like. Therefore, in consideration of the workability in the secondary processing of the Pt—W alloy, an upper limit of the W concentration is set to 15 mass %.

Although there is no need to especially limit a method for measuring the W concentration in a Pt—W alloy, inductively coupled plasma emission spectral analysis (ICP emission spectral analysis), X-ray fluorescence analysis (XRF analysis) or the like can be applied. In the ICP emission spectral analysis, a Pt—W alloy is made into a thin wire or cut into small pieces, and liquefied with hydrofluoric acid, and the resultant solution is analyzed with an ICP emission spectral analyzer. In the XRF analysis, a Pt—W alloy sample is embedded in a conductive resin, a cross section of the resultant resin is polished, and the resultant cross sectional portion is analyzed with an XRF analyzer. Besides, a principal component of a Pt—W alloy can be easily measured not only by these analysis methods but also by another analysis method such as energy dispersive X-ray analysis (EDX) or wavelength dispersive X-ray analysis (WDX).

In addition, in the medical Pt—W alloy of the present invention, a Zr concentration should be 1000 ppm or less. As described above, Zr forms a minute precipitate in the Pt—W alloy, and thus degrades workability of the alloy, and therefore, the content is limited in the present invention. The Zr content is preferably 800 ppm or less, and more preferably 500 ppm or less. Although detailed description will be given later, Zr is mixed into the alloy when a Zr containing crucible is used during the production procedures of the Pt—W alloy, particularly in a casting step. The Zr concentration of 1000 ppm or less can be attained by suppressing mixture of Zr in the casting step. It is noted that a lower limit of the Zr content is preferably 0 ppm, but a realistic lower limit is preferably about 10 ppm.

Besides, in addition to Zr, Ca is another impurity element to be preferably regulated. Zr affects the workability of the Pt—W alloy not only during cold working but also at a stage of hot working. Ca is preferably limited for improving workability mainly in cold working. Specifically, a Ca content is preferably 250 ppm or less, and more preferably 100 ppm or less. Also a lower limit of the Ca content is preferably 0 ppm, but a realistic lower limit is preferably about 0.1 ppm. It is noted that the regulation of the Ca content is not essential. When cold working needs to be performed at a high degree of processing, for example, when it is necessary to produce an extra fine wire having a processing rate beyond 99%, the regulation of the Ca content is effective.

The contents of Zr and Ca are preferably measured by glow discharge mass spectrometry (GD-MS analysis). Such impurity elements are preferably analyzed as accurately as possible without being affected by other elements. In GD-MS analysis, a Pt—W alloy sample is embedded in a resin, a cross section of the resultant resin is polished, and the resultant cross sectional portion is analyzed with a GD-MS analyzer.

The Pt—W alloy of the present invention substantially contains Pt and W, and a balance excluding W corresponds to Pt. However, inevitable impurities can be contained. As the inevitable impurities, Mg (magnesium), Al (aluminum), Si (silicon), Ni (nickel), Ti (titanium), Fe (iron), Cu (copper), Ag (silver), Au (gold), Y (yttrium), Ir (iridium), Pd (palladium), Ru (ruthenium), Rh (rhodium) and the like may be contained. A total content of such impurities is preferably 0.5 mass % or less, and more preferably 0.2 mass % or less. It is noted that the content of inevitable impurities may be varied depending on a method for producing the Pt—W alloy (melting casting step) described below. For example, when a crucible is used in the melting casting step, the crucible contains, in many cases, at least one of the above-described elements in an amount of 1 ppm or more. For measuring the contents of these inevitable impurities, a known analysis method such as the ICP analysis, the XRF analysis and the GD-MS analysis described above can be appropriately applied.

The method for producing the medical Pt—W alloy of the present invention is basically the same as a conventional method for producing a Pt—W alloy, and the Pt—W alloy is produced from raw material metals of Pt and W through the melting casting step. In the present invention, however, it is necessary to set the Zr content in the alloy to 1000 ppm or less. According to examination made by the present inventors, mixture of Zr in a Pt—W alloy is caused mainly because of a zirconia crucible used in preparing a Pt—W alloy melt by melting casting.

A zirconia crucible (hereinafter sometimes simply referred to as a crucible) is a ceramic crucible that contains zirconia ($ZrO_2$) as a principal component, and further contains one or more stabilizers such as calcium oxide (CaO) and yttria ($Y_2O_3$). A zirconia crucible is known as a heat-resistant container excellent in thermal stability/corrosion resistance, resistant to erosion by a melt, and minimally contaminated with a melt. Therefore, a zirconia crucible is generally used in melting a metal having a high melting point such as platinum. In the present invention, use of a zirconia crucible is not completely avoided, but a zirconia crucible is appropriately used to regulate the Zr content in the resultant Pt—W alloy.

An alloy melt of the Pt—W alloy is prepared by heating the raw material metals in a crucible. At this point, Pt metal and W metal or a W compound are used as the raw material metals, and these are mixed/melted to obtain a desired composition, and thus, the alloy melt can be obtained. Alternatively, a Pt—W alloy to be used as a mother alloy may be precedently prepared, and metal Pt or the like may be appropriately mixed with the mother alloy for composition adjustment to melt the resultant. In the melting casting step, the crucible is heated to completely melt the raw material metals to obtain an alloy melt, and the alloy melt is casted in a mold to obtain an alloy ingot. Alternatively, the crucible may be directly used as a mold to produce an alloy ingot. For the heating in melting, any of conventional melting methods for a Pt alloy such as a high frequency induction heating method or an electric heating method can be employed.

Here, in the present invention, a retention time from generation of the alloy melt is adjusted. Thus, a reaction on an interface between the inner wall of the crucible and the melt is controlled to avoid the mixture of Zr and to set the Zr content in the resultant Pt—W alloy in the above-described range. In the present invention, the retention time of the alloy melt refers to a time from a time when the respective raw materials are completely melted to generate the alloy melt until a time when heating of the melt (crucible) is stopped. For example, in employing the high frequency induction heating method, the retention time corresponds to a time from the generation of the melt until heating output is stopped. It is noted that the timing of the generation of the melt can be determined by temperature measurement with a radiation thermometer, or by visually observing state change. In the production of the Pt—W alloy of the present invention, the retention time of the alloy melt is preferably 60 seconds or less, and more preferably 30 seconds or less.

In this manner, in the present invention, the use of a zirconia crucible itself is not avoided. This is because, for producing the Pt—W alloy by comparatively efficiently performing the melting casting step, the use of a zirconia crucible is suitable. It goes without saying, however, that the melting casting step can be performed without using a zirconia crucible. For example, when a water-cooled copper mold is used, an ingot of a Pt—W alloy can be produced with mixture of various impurity elements including Zr avoided.

Besides, in addition to process control in the melting casting step as described above, it is also preferable to use a raw material metal having a Zr content falling in the above-described range. It is noted that the raw material selection and the process control in the melting casting step contribute to not only the reduction of the Zr content but also reduction of the Ca content. This is because Ca is also contained in a zirconia crucible in some cases.

Procedures following the control of the melt in the melting casting step are the same as conventional production procedures for a Pt—W alloy. After producing the alloy ingot in the melting casting step, the ingot can be processed into a shape and a dimension as needed through hot working and cold working. Besides, a heating treatment such as annealing can be performed.

The Pt—W alloy of the present invention can be provided as a medical material in any of various shapes such as a plate, a bar/square bar/tubular bar, and a wire. Many of medical tools such as a stent, an embolic coil, and a guide wire are in the shape of a wire or a weaved wire. The Pt—W alloy of the present invention can be supplied/used in the shape of a wire owing to the effect of improving workability.

The medical Pt—W alloy of the present invention described so far can be used as at least a part of any of various medical tools. Examples of the medical tool in which the present invention is useful include a stent such as a flow diverter stent or a stent retriever, a catheter such as a balloon catheter, a coil such as an embolic coil, a guide wire, dental braces, a clasp, an artificial tooth root, a clip, a staple, a bone plate, a nerve stimulation electrode, a lead for a pacemaker, and a radiation marker. Among these examples, a stent such as a flow diverter stent is a medical tool for improving blood flow in a cerebral aneurysm, and is produced by weaving a wire with a knitting machine. An embolic coil is a tool to be filled in a cerebral aneurysm for embolization of an aneurysm foramen, and is produced by processing a wire into a coil shape with a winding machine. A stent retriever is produced by producing a pipe material/tube material, and subjecting the resultant to laser processing for molding.

Advantageous Effects of Invention

As described so far, a medical Pt alloy of the present invention has an effect of improving workability as compared with a known Pt—W alloy. As a result, in production of various medical tools in the shape of a fine wire, an alloy wire can be efficiently produced in a high yield.

BRIEF DESCRIPTION OF THE DRAWING

The FIGURE illustrates an SEM image of a cross section of a Pt-12 mass % W alloy (melt retention time: 3 min) produced in First Embodiment.

DETAILED DESCRIPTION OF THE PREFERRED EMBODIMENTS

First Embodiment: A preferred embodiment of the present invention will now be described. In the present embodiment, a commercially available zirconia crucible was used to produce Pt—W alloy ingots having various compositions for evaluating workability in hot working. In the present embodiment, a Pt—W alloy (W concentration: 10 mass %, or 12 mass %) was produced precedently with a water-cooled copper mold, and this alloy was used as a mother alloy to be melted again in a zirconia crucible, and thus, Pt—W alloy ingots having the same composition were produced. The mother alloy was thus melted again to obtain alloy ingots for making melting conditions uniform among samples by using the alloys in the uniform state, and for concentrating a factor of mixture of impurities (such as Zr) to a melt retention time.

For producing each Pt—W alloy ingot, 240 g of the mother alloy was put in a commercially available zirconia crucible (product name: ZIR, capacity: 70 cc), and the resultant was heated in a high frequency melting apparatus under a reduced-pressure argon atmosphere. It was confirmed that the metal had been melted to form a melt, and a melt retention time from this time point until the output of the melting apparatus was stopped was adjusted. After stopping the output, the resultant was casted in a Cu mold over about 2 seconds using an automatic casting function of the melting apparatus. An ingot (dimension: diameter of 11 mm×length of 70 mm) produced by cooling the resultant to normal temperature was taken out of the mold. In the present embodiment, Pt-10 mass % W alloys (Example 1 and Comparative Example 1) respectively having the melt retention time set to 30 seconds and 1 minute, and Pt-12 mass % W alloys (Example 2 and Comparative Example 2) respectively having the melt retention time set to 30 seconds and 3 minutes were produced.

Thereafter, each of the ingots of the Pt—W alloys of the respective compositions thus produced was heated at 700° C., and then subjected to hot swaging at a processing rate of 15%, and workability was evaluated based on whether or not a processed sample (dimension: diameter of 9.5 mm×length of 80 mm) had a crack on the surface. A crack was checked visually and with a microscope, and when no crack was found in the entire sample, the sample was evaluated acceptable (good), and when even one crack was found, the sample was evaluated as unacceptable (poor). Besides, a sample in which no crack had been caused through hot working was subjected to cold swaging at room temperature at a processing rate of 15%, and then, similarly evaluated for whether or not a crack was caused.

It is noted that each Pt—W alloy was measured for a Zr content and a Ca content with a glow discharge mass analyzer (GD-MS, name of apparatus: Astrum) after producing the ingot. The measurement results and evaluation results are shown in Table 1.

TABLE 1

| | Alloy composition | Melt retention time | Zr content | Ca content | Workability in hot working | Workability in cold working |
|---|---|---|---|---|---|---|
| Example 1 | Pt-10% W | 30 sec | 100 ppm | 1 ppm | good | good |
| Comparative Example 1 | | 1 min | 200 ppm | 3 ppm | good | good |
| Example 2 | Pt-12% W | 30 sec | 90 ppm | 1 ppm | good | good |
| Comparative Example 2 | | 3 min | 1050 ppm | 30 ppm | poor | — |

It is understood from Table 1 that a Zr content corresponding to a component of the crucible is changed by adjusting the melt retention time in the crucible. It was confirmed that when the Zr content exceeds 1000 ppm, the workability was poor and a crack was caused on the surface even through hot working. On the other hand, a Pt—W alloy having a Zr content of 1000 ppm or less did not have a crack caused through hot working, and in addition, did not have a crack caused through cold working.

The FIGURE illustrates an SEM image (COMPO image) of the cross section of the Pt-12 mass % W alloy (melt retention time: 3 min) in which a crack was found. It is understood from the FIGURE that particles presumed as precipitates were randomly found on a grain boundary and in a grain in the Pt—W alloy having a high Zr content. This observation region was subjected to EDX analysis, and as a result, Pt, Zr and O were detected in positions of the precipitates. In EDX, peak positions of Pt and Zr are close to each other, and hence attention was paid to a detection position of O, and the detection position of O overlapped the position of the precipitate, and thus, it was presumed that the precipitate was an oxide (Zr oxide).

Second Embodiment: In the present embodiment, Pt—W alloys were produced with a water-cooled copper mold used in the melting casting step and with Zr added to adjust the content. A Pt-10% W mother alloy prepared in the same manner as in First Embodiment was used, and was placed in a water-cooled copper mold together with Zr metal (purity of 99%) (total amount charged: 100 g). Thereafter, a melt was prepared by arc melting to produce an alloy ingot. In the present embodiment, the amount of Zr charged was set to 50 ppm, 100 ppm, 250 ppm, 500 ppm, 1000 ppm, or 1500 ppm in the Pt-10 mass % W alloy. It is noted that the amount of Zr charged and the Zr content (analysis value) in the produced alloy ingot do not accord with each other as described above. This is probably due to volatilization of the raw materials during melting, and in the present embodiment, evaluation was made based on the Zr content in the alloy ingot.

The Pt-10 mass % W alloy having different Zr contents thus produced were subjected to hot working and cold working in the same manner as in First Embodiment, and were evaluated for workability. Besides, in each of the alloy ingots, the Zr content was analyzed by GD-MS. The workability evaluation results thus obtained are shown in Table 2.

TABLE 2

| | Alloy composition | Zr Content Amount charged | Zr Content Analysis value | Workability in hot working | Workability in cold working |
|---|---|---|---|---|---|
| Example 4 | Pt-10% W | 50 ppm | 45 ppm | good | good |
| Example 5 | | 100 ppm | 80 ppm | good | good |
| Example 6 | | 250 ppm | 240 ppm | good | good |
| Example 7 | | 500 ppm | 365 ppm | good | good |
| Example 8 | | 1000 ppm | 880 ppm | good | good |
| Comparative Example 4 | | 1500 ppm | 1150 ppm | poor | — |

Ca content: substantially 0 ppm

In the present embodiment, the Pt—W alloys with the Zr content intentionally adjusted were examined, and as shown in Table 2, a crack caused through hot working was observed in the Pt-10 mass % W alloy having a Zr content exceeding 1000 ppm. This result matches the result obtained in First Embodiment.

Third Embodiment: In the present embodiment, Pt-10 mass % W alloys were produced with a water-cooled copper mold used in the same manner as in Second Embodiment and with a Ca content adjusted. A mother alloy similar to that used in Second Embodiment was used, and was placed in a water-cooled copper mold together with a Ca powder (purity of 99%) (total amount charged: 100 g). Thereafter, a melt was prepared by arc melting to produce an alloy ingot. In the present embodiment, the Pt-10 mass % W alloys were produced with the amount of Ca charged set to 25 ppm, 50 ppm, 100 ppm, 250 ppm, 500 ppm, or 750 ppm. It is noted that the amount charged and an analysis value in the alloy ingot do not accord with each other also with respect to Ca due to volatilization during melting.

The Pt-10 mass % W alloys having different Ca contents produced in the present embodiment were subjected to hot working and cold working in the same manner as in First Embodiment, and was evaluated for workability in these processing. It is noted that the Ca content in each alloy ingot was analyzed by GD-MS. The workability evaluation results thus obtained are shown in Table 3.

TABLE 3

| | Alloy composition | Ca content | | Workability in hot working | Workability in cold working |
| | | Amount charged | Analysis value | | |
|---|---|---|---|---|---|
| Example 9 | Pt-10% W | 25 ppm | 10 ppm | good | good |
| Example 10 | | 50 ppm | 13 ppm | good | good |
| Example 11 | | 100 ppm | 62 ppm | good | good |
| Example 12 | | 250 ppm | 145 ppm | good | good |
| Example 13 | | 500 ppm | 188 ppm | good | good |
| Comparative Example 5 | | 750 ppm | 285 ppm | good | poor |

Zr content: substantially 0 ppm

As shown in Table 3, it was confirmed that even when Ca was contained in an amount beyond 250 ppm, a crack was not caused in hot working but was caused in cold working. It is deemed, based on this result, that Ca has a high possibility of affecting workability in cold working of a Pt—W alloy.

In First Embodiment using a zirconia crucible, the amount of Ca mixed was small even when the melt retention time was rather long (3 min). It is thus deemed that there is a lower possibility of excessive mixture of Ca than mixture of Zr. However, Ca is added to a constituent material of a crucible as a stabilizer, and hence mixture of a large amount of Ca may be of concern depending on the amount added (and through repeated melting operations). Besides, in some production sites, Pt alloy pieces removed in cutting processing or the like may be melted again to be used in some cases. In consideration of the variations of the composition of a crucible, and viewpoint of ensuring product cost/efficiency, when a zirconia crucible is used, the melt retention time should be noted for suppressing mixture of Zr and Ca.

Fourth Embodiment: In the present embodiment, a plurality of Pt—W alloys having different W concentrations were produced through procedures similar to those employed in First Embodiment, and wires were produced therefrom through hot working and cold working. Then, the wires thus produced were subjected to coiling processing (secondary processing) to evaluate workability in the processing.

For producing the Pt—W alloys, in the same manner as in First Embodiment, mother alloys (W concentration: 8 mass %, 10 mass %, 12 mass %, 15 mass %, and 16 mass %) of the Pt—W alloys were produced with a water-cooled copper mold used, and each of the mother alloys was melted again in a zirconia crucible to produce a Pt—W alloy ingot. Conditions for melting casting with the zirconia crucible were the same as those employed in Example 1 (melt retention time: 30 seconds). Then, the thus produced alloy ingot was heated at 700° C. for 10 minutes, and molded into a crude wire having a wire diameter of 3.5 to 7.4 mm through hot swaging. Next, the crude wire was subjected to cold wire drawing at room temperature to be processed into a wire diameter of 0.5 mm, and at this point, a process annealing treatment was performed by heating at 800° C. for 60 minutes under a nitrogen atmosphere. After the annealing, the resultant was further subjected to cold wire drawing to be processed into a Pt alloy wire having a wire diameter of 28 μm. It is noted that a Zr content obtained after the casting with the zirconia crucible was 100 ppm or less in all the alloy ingots.

Through the hot/cold working described above, no crack/disconnection was caused in the materials to be processed. This is probably because the mixture of Zr was suppressed by applying the melting casting step similar to that of First Embodiment, and appropriately setting the retention time of the alloy melt.

Each of the Pt—W alloy fine wires (wire diameter of 28 μm) thus produced was measured for hardness on a cross section with a Vickers hardness measuring device (product name: HM-200, manufactured by Mitutoyo Corporation, load: 50 gf). Besides, a tensile testing machine for extra fine wires (Strograph E3-S: Toyo Seiki Seisaku-sho, Ltd.) was used to perform a tensile test for measuring tensile strength (UTS).

Then, each of the Pt—W alloy wires thus produced was subjected to coiling processing for evaluating workability in secondary processing. This evaluation was made depending on whether or not disconnection was caused during the coiling processing. For the coiling processing, a spring index (coil average diameter (D)/filament diameter (d)) was set to 4.5, and the wire was wound around a core material (diameter of 0.1 mm) for the processing. When an alloy wire with a length of m could be processed to the last through the coiling processing, this sample was determined to have good workability (good). When a wire was disconnected during the processing, the processing was terminated at that point, and this sample was determined to have poor workability (poor). Measurement results and evaluation results obtained in the present embodiment are shown in Table 4.

TABLE 4

| | | Mechanical properties | | Evaluation of secondary processing workability |
|---|---|---|---|---|
| No. | Alloy composition | Hardness | Tensile strength | |
| Example 14 | Pt-8% W | 368 Hv | 2450 Mpa | good |
| Example 15 | Pt-10% W | 455 Hv | 2783 Mpa | good |
| Example 16 | Pt-12% W | 498 Hv | 2996 Mpa | good |

TABLE 4-continued

| No. | Alloy composition | Mechanical properties | | Evaluation of secondary processing workability |
| --- | --- | --- | --- | --- |
| | | Hardness | Tensile strength | |
| Example 17 | Pt-15% W | 550 Hv | 3159 Mpa | good |
| Comparative Example 6 | Pt-16% W | 605 Hv | 3359 Mpa | poor |

As described above, even when a Zr concentration in a Pt—W alloy exceeds 15 mass %, the alloy can be processed into a wire by suppressing Zr mixture. A Pt—W alloy wire having a W concentration of 16 mass % was, however, disconnected during secondary processing (coil processing). W contained in a Pt—W alloy contributes to strength increase of the alloy. This can be confirmed also from the measurement results of the mechanical properties shown in Table 4. Excessively high strength/hardness affects, however, workability in secondary processing. In consideration of the usage of the Pt—W alloy of the present invention, it was confirmed that an upper limit of the W concentration should be 15 mass %. Regarding a lower limit of the W concentration, it is not that an alloy wire having a W concentration of 8 mass % has low strength/hardness, but with a reference standard set to a hardness value of 400 Hv (tensile strength of 2500 MPa), it was confirmed that the W concentration is adequately 10 mass % or more.

INDUSTRIAL APPLICABILITY

As described above, a medical Pt—W alloy of the present invention is excellent in workability, and an alloy ingot of this alloy can be easily processed into alloy materials in various shapes. In particular, workability in processing into a wire is also excellent, and hence, the Pt—W alloy can be applied to various tools in the shape of a wire. Besides, the Pt—W alloy of the present invention is good also in mechanical properties and X-ray visibility. Owing to these advantages, the present invention can be expected to be used in a medical tool such as an embolic coil or a guide wire.

What is claimed is:

1. A medical Pt—W alloy, comprising 10 mass % or more and 15 mass % or less of W, with the balance being Pt and inevitable impurities,
wherein the alloy further comprises Zr and a content of Zr in the alloy is 10 ppm or more and 800 ppm or less.

2. The medical Pt—W alloy according to claim 1, wherein a content of Ca in the alloy is 250 ppm or less.

3. A medical tool, comprising the medical Pt—W alloy defined in claim 2.

4. A medical tool, comprising the medical Pt—W alloy defined in claim 1.

5. The medical tool according to claim 4, wherein the medical tool is any one of a stent, a catheter, a coil, a guide wire, a delivery wire, dental braces, a clasp, an artificial tooth root, a clip, a staple, a bone plate, a nerve stimulation electrode, a lead for a pacemaker, and a radiation marker.

* * * * *